US012515003B2

(12) United States Patent
Haibach

(10) Patent No.: US 12,515,003 B2
(45) Date of Patent: Jan. 6, 2026

(54) CUSTOMIZABLE MASK AND METHOD OF SIZING

(71) Applicant: KONINKLIJKE PHILIPS N.V., Eindhoven (NL)

(72) Inventor: Richard Thomas Haibach, Verona, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 881 days.

(21) Appl. No.: 17/831,586

(22) Filed: Jun. 3, 2022

(65) Prior Publication Data

US 2022/0288338 A1 Sep. 15, 2022

Related U.S. Application Data

(62) Division of application No. 16/142,749, filed on Sep. 26, 2018, now Pat. No. 11,376,386.

(60) Provisional application No. 62/565,567, filed on Sep. 29, 2017.

(51) Int. Cl.
*A61M 16/06* (2006.01)

(52) U.S. Cl.
CPC . *A61M 16/0622* (2014.02); *A61M 2016/0661* (2013.01); *A61M 16/0666* (2013.01)

(58) Field of Classification Search
CPC .......... A61M 2016/0661; A61M 16/06; A61M 16/0605; A61M 16/0611; A61M 16/0616; A61M 16/0622; A61M 16/0666
See application file for complete search history.

(56) References Cited

U.S. PATENT DOCUMENTS

| | | | | |
|---|---|---|---|---|
| 2,228,502 | A | 1/1941 | Boothby | |
| 7,562,658 | B2 | 7/2009 | Madaus | |
| 7,971,590 | B2 | 7/2011 | Frater | |
| 8,522,784 | B2 | 9/2013 | Ng | |
| 10,369,314 | B2 | 8/2019 | Chodkowski | |
| 11,376,383 | B2 | 7/2022 | Beane | |
| 2007/0131229 | A1 | 6/2007 | Madaus | |
| 2012/0080035 | A1* | 4/2012 | Guney | A61M 16/0616 128/205.25 |
| 2012/0285455 | A1 | 11/2012 | Varga | |
| 2014/0345621 | A1* | 11/2014 | Zack | A61M 16/06 29/428 |

(Continued)

FOREIGN PATENT DOCUMENTS

| | | | |
|---|---|---|---|
| WO | 2016000040 | A1 | 1/2016 |
| WO | 2016032343 | A1 | 3/2016 |
| WO | 2017108763 | A1 | 6/2017 |

*Primary Examiner* — Joseph D. Boecker
(74) *Attorney, Agent, or Firm* — Michael W. Haas

(57) ABSTRACT

A mask for use in providing a flow of a treatment gas to the airway of a user. The mask includes a frame and a conformable seal which is structured to sealingly engage about at least one of at least a portion of nose or mouth of the user. The frame includes a front face and a concave shaped rear face which faces the user when the mask is disposed on the user's face. The rear face defines a cavity which is structured to receive at least one of a portion of a nose and/or mouth of the user therein. The frame also includes a number of deformable zones, each deformable zone being structured to receive a removable insert. Each deformable zone is structured to adapt to at least one of a size or shape of the removable insert received therein.

9 Claims, 5 Drawing Sheets

(56) References Cited

U.S. PATENT DOCUMENTS

| | | | | |
|---|---|---|---|---|
| 2015/0007439 | A1 | 1/2015 | Todd | |
| 2015/0040909 | A1* | 2/2015 | Willard ............. | A61M 16/0616<br>128/205.25 |
| 2015/0314097 | A1 | 11/2015 | Kwok | |
| 2016/0166793 | A1 | 6/2016 | Mclaren | |
| 2016/0287828 | A1* | 10/2016 | Harrison ........... | A61M 16/0816 |
| 2016/0310687 | A1 | 10/2016 | Mcauley | |

* cited by examiner

CUSTOMIZABLE MASK AND METHOD OF SIZING

CROSS-REFERENCE TO RELATED APPLICATIONS

This patent application is a divisional of U.S. application Ser. No. 16/142,749, filed Sep. 26, 2018, which claims the priority benefit under 35 U.S.C. § 119(e) of U.S. Provisional Application No. 62/565,567, filed on Sep. 29, 2017, the contents of which are herein incorporated by reference.

BACKGROUND OF THE INVENTION

1. Field of the Invention

The present invention pertains to a customizable mask for use in providing a flow of a treatment gas to the airway of a user. The present invention also relates to methods of sizing and providing such masks to a user.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

Obtaining a proper fitting mask for an individual patient is critical in order to optimize patient adherence to a prescribed therapy, as well as to optimize such therapy itself. In attempting to provide a best fitting mask, equipment providers typically provide various sizes of each mask design. While such solution is generally cost effective, it is far from perfect, particularly for individuals with facial geometries that stray from typical "average" faces which are generally used for modeling of such masks.

A more costly approach is to have a "custom" mask produced for an individual. Current state-of-the-art systems for creating a "custom" mask for a patient for use in delivering a flow of a treatment gas to the patient use a 3-dimensional (3D) scan as input to create a model, which is used as a reference for creating the custom mask. Such approach requires costly equipment and can take several hours to produce a mask. Hence, there is still room for improvement over such "custom" masks.

SUMMARY OF THE INVENTION

Embodiments of the present invention provide solutions for providing a patient (hereinafter, a "user") with a customized mask that is both less expensive than other solutions and can be produced quickly in varying quantities as needed. Embodiments of the present invention also allow for a custom mask to be readily re-customized as needed, a feature presently unavailable in "custom" masks.

As one aspect of the invention, a mask for use in providing a flow of a treatment gas to the airway of a user is provided. The mask comprises a frame having: a front face positioned to face away from the user when the mask is disposed on the face of the user; a concave shaped rear face positioned to face toward the user when the mask is disposed on the face of the user, the rear face defining a cavity, the cavity being structured to receive the flow of the treatment gas therein and to receive at least one of a portion of a nose of the user and a mouth of the user therein; an opening defined in a central portion of the frame, the opening passing between the front face and the rear face, the opening being structured to have a conduit coupled thereto for receiving the flow of the treatment gas; and a number of deformable zones defined in the frame, each deformable zone being structured to receive a removable insert, each deformable zone being structured to adapt to at least one of a size or a shape of the removable insert received therein. The mask also comprises a conformable cushion coupled to the frame and structured to sealingly engage about at least one of at least a portion of the nose or the mouth of the user.

Each deformable zone may be formed from a first material, and the remainder of the frame may be formed from a second material different than the first material. The second material may be more rigid than the first material. The number of deformable zones may comprise a plurality of deformable zones, wherein each deformable zone comprises a portion of a unitary piece of the first material. The first material may comprise a silicone material and the second material may comprise a plastic.

The frame may be formed from a first material and each deformable zone may be formed as a thinned region in the first material. The first material may have a first thickness in the thinned region and a second thickness greater than the first thickness outside of the deformable zone.

The number of deformable zones may comprise only one deformable zone disposed at or about a portion of the frame which is structured to be disposed at or about the nose of the user when the mask is disposed on the user.

The number of deformable zones may comprise: a first deformable zone disposed at or about a portion of the frame which is structured to be disposed at or about the nose of the user when the mask is disposed on the user; and a second deformable zone disposed on an opposing side of the opening from the first deformable zone.

The number of deformable zones may comprise: a first deformable zone disposed at or about a portion of the frame which is structured to be disposed at or about the nose of the user when the mask is disposed on the user; a second deformable zone disposed about 180° about the opening from the first deformable zone; a third deformable zone disposed about 90° about the opening from the first deformable zone; and a fourth deformable zone disposed about 270° about the opening from the first deformable zone.

The frame may further comprise a number of removable inserts, each removable insert selectively coupled in a deformable zone.

As another aspect of the invention, a method of sizing a customized mask to a user is provided. The method comprises: identifying a number of characteristics of the user; determining a number of inserts for the user based on the number of characteristics; and identifying the number of inserts to the user.

Identifying the number of inserts to the user may comprise providing the number of inserts to the user.

Providing the number of inserts to the user may comprise: installing the number of inserts in a frame of the mask; and providing the mask to the user. Installing the number of inserts in a frame of the mask may comprise sliding each insert into the frame. Installing the number of inserts in a frame of the mask may comprise snapping each insert into the frame.

Identifying a number of characteristics of the user may comprise obtaining information from the user. The information may comprise a number of facial dimensions of the user. The number of facial dimensions of the user may be obtained by questioning the patient regarding dimensional information. The number of facial dimensions of the user may be obtained by performing a facial scan of the user.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1A:
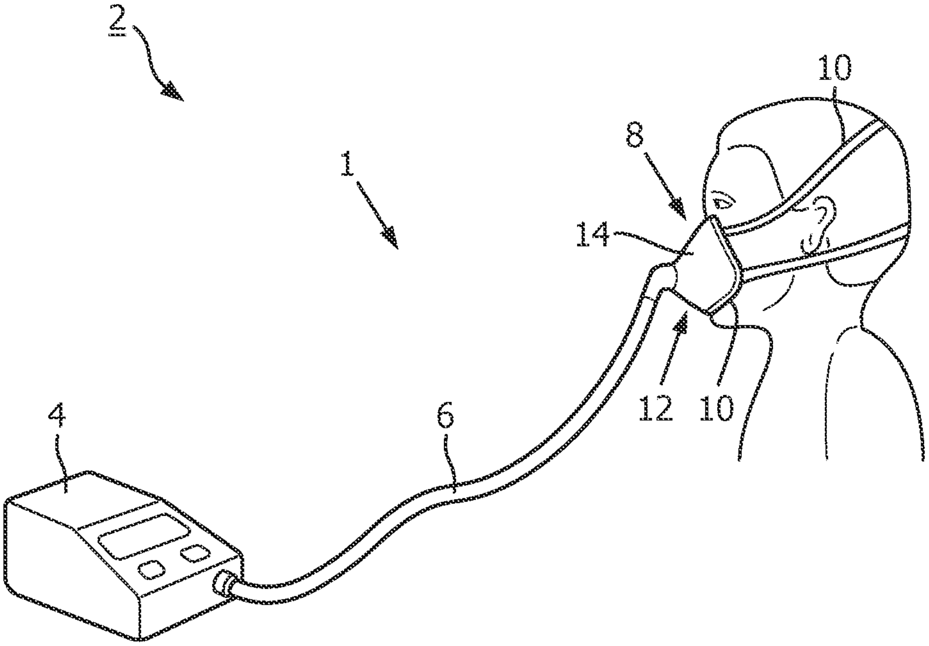
FIG. 1A is a simplified diagram of an airway pressure support system according to an example embodiment of the present invention which is operated within an environment, such as a bedroom or home of the user of airway pressure support system, shown with a patient interface device thereof disposed on the face of a patient.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As used herein, the statement that two or more parts or components "engage" one another shall mean that the parts exert a force against one another either directly or through one or more intermediate parts or components. As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Embodiments of the present invention provide for a collapsible conduit and/or frame which can be readily inflated and create structure through which CPAP therapy air may flow. Even during the event of a power loss, the conduit and/or frame will remain inflated, maintain its shape, and allow airflow therethrough.

An example airway pressure support system 2 shown in simplified form according to one particular, non-limiting exemplary embodiment of the present invention which is operated within an ambient environment 1, such as, without limitation, a bedroom or home of the user of airway pressure support system 2 is shown in FIG. 1. System 2 includes a pressure/flow generator 4, a delivery conduit 6, a patient interface device 8 structured to engage about an airway of the patient, and a headgear 10 for securing patient interface device 8 to the head of a patient (not numbered). Pressure generating device 4 is structured to generate a flow of breathing gas which may be heated and/or humidified. Pressure generating device 4 may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pennsylvania), and auto-titration pressure support devices. Delivery conduit 6 is structured to communicate the flow of breathing gas from pressure generating device 4 to patient interface device 8. Delivery conduit 6 and patient interface device 8 are often collectively referred to as a patient circuit.

A BiPAP® device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. For present purposes, pressure/flow generating device 4 is also referred to as a gas flow generating device, because flow results when a pressure gradient is generated. The present invention contemplates that pressure/flow generating device 4 is any conventional system for delivering a flow of gas to an airway of a patient or for elevating a pressure of gas at an airway of the patient, including the pressure support systems summarized above and non-invasive ventilation systems. Although described herein in example embodiments wherein a pressurized flow of gas is utilized, it is to be appreciated that embodiments of the invention as described herein could also be readily employed in other generally non-pressurized applications (e.g., without limitation, in high flow therapy applications).

In the exemplary embodiment, patient interface device 8 includes a patient sealing assembly or mask 12, which in the illustrated embodiment is a full face mask. It is to be appreciated, however, that other types of patient sealing assemblies, such as, without limitation, a nasal mask, or alternative cradle or pillows mask, may be substituted for mask 12 while remaining within the scope of the present invention. It is also to be appreciated that headgear 10 is provided solely for exemplary purposes and that any suitable headgear arrangement may be employed without varying from the scope of the present invention.

Figure 1B:
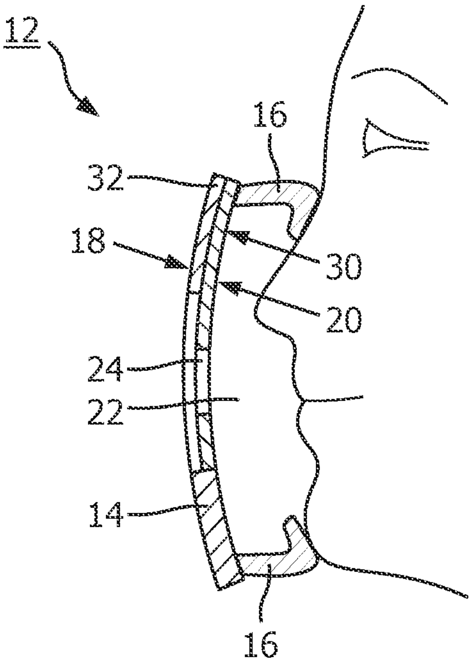
FIG. 1B is an enlarged sectional view of mask of FIG. 1B shown in greater detail disposed on the face of a patient taken along a mid-plane of the mask of FIG. 1A.

Referring to FIG. 1A, and the enlarged detail sectional view of FIG. 1B, mask 12 includes a frame 14 and a conformable cushion 16 coupled to frame 14. Frame 14 includes a generally convex shaped front face 18 which faces generally away from the patient when mask 12 is disposed on the face of the patient and a generally concave shaped rear face 20 which faces generally toward the patient when mask 12 is disposed on the face of the patient. Conformable cushion 16 is structured to sealingly engage about at least one of at least a portion of the nose or the mouth of the user (i.e., so as to form a combination oral nasal mask such as shown in FIGS. 1A and 1B, or a nasal mask which only covers a user's nose). Rear face 20 along with conformable cushion 16 define a cavity 22 (FIG. 1B) which is structured to receive the flow of the treatment gas therein and to receive at least one of a portion of a nose of the user and a mouth of the user therein.

Frame 14 further includes an opening 24 defined in a central portion (not numbered) of frame 14. Opening 24 passes between front face 18 and rear face 20. Opening 24 is structured to have a conduit, such a delivery conduit 6 of FIG. 1A, coupled thereto, for receiving the flow of the treatment gas from delivery conduit 6 into cavity 22 before passing to an airway of the user.

Figure 2:
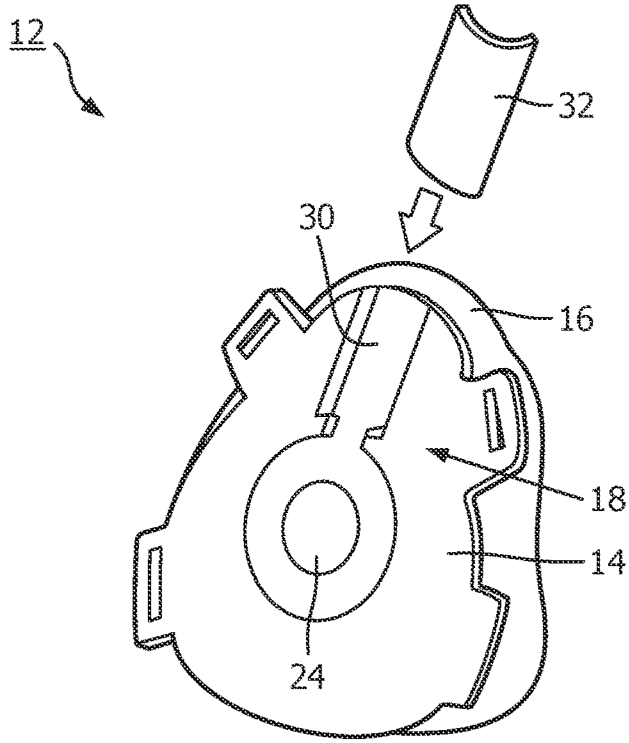
FIG. 2 is a partially exploded isometric view of the mask of FIG. 1B shown with a single removable insert exploded away from the frame of the mask.

Referring now to FIG. 2, which shows a partially exploded isometric view of mask 12, frame 14 further includes a deformable zone 30 defined in frame 14 at or about a portion of frame 14 which is structured to be disposed at or about the nose of the user when the mask is disposed on the user (such as shown in FIG. 1B). Deformable zone 30 is structured to receive a removable insert 32, which is shown exploded from deformable zone 30, which is then selectively coupled in deformable zone 30. In the example embodiment shown in FIG. 2, insert 32 is generally slidable into deformable zone 30 (in a direction such as shown by the arrow in FIG. 2). In other example embodiments of the present invention such insert may be generally "snapped" into a corresponding deformable zone by pressing an insert toward front face 18. It is also to be generally appreciated that generally any suitable arrangement for coupling an insert with a deformable zone may be employed without varying from the scope of the present invention.

Continuing to refer to FIG. 2, deformable zone 30 is structured to adapt to at least one of a size or a shape of removable insert 32 when insert 32 is received in deformable zone 30. In the example embodiment of FIG. 1B and FIG. 2, deformable zone 30 is formed solely from a first, generally flexible material (e.g., without limitation, silicone) and the remainder of frame 14 is formed from a second material which is different, and typically more rigid, than the first material. In the example embodiment of the present invention shown in FIGS. 1B and 2, a rigid plastic was employed as the second material with a silicone material employed as the first material. In such example, a layer of the silicone material forms generally the entire patient facing side of frame 14 (and thus also rear face 20). It is to be appreciated that such arrangement allows for selective deformation of deformable zone 30 by inserting insert 32 in deformable zone 30.

Figure 3A:
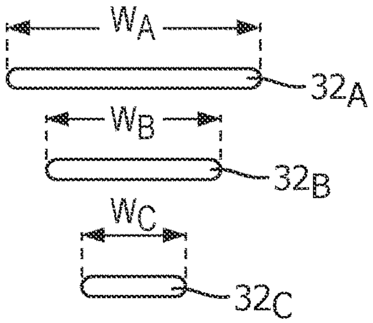
FIG. 3A shows, in simplified form, end views of three inserts of varying width according to an example embodiment of the present invention.
Figure 3B:
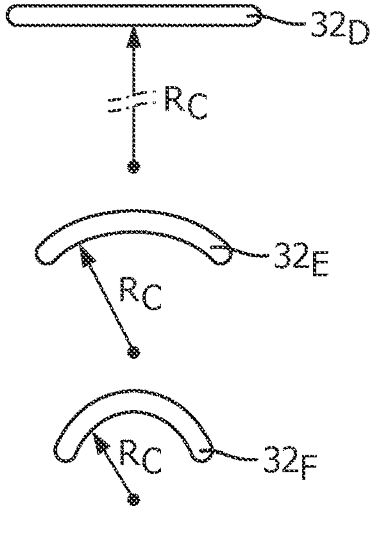
FIG. 3B shows, in simplified form, end views of three inserts of varying curvature according to an example embodiment of the present invention.
Figure 4A:
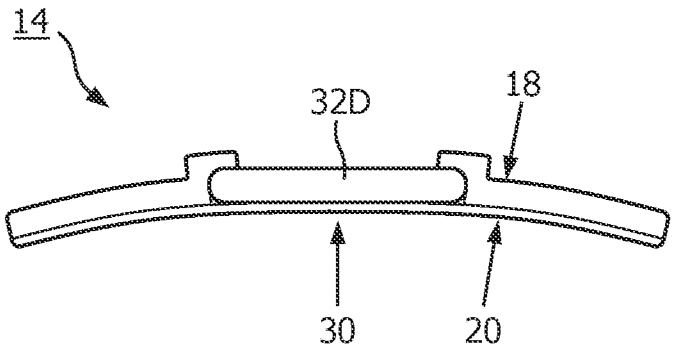
FIGS. 4A-4C, respectively, show, in simplified, slightly exaggerated form, top views of the frame of the mask of FIG. 2 with different ones of the three inserts of varying curvature of FIG. 3B installed in the deformable zone of the frame.
Figure 4B:
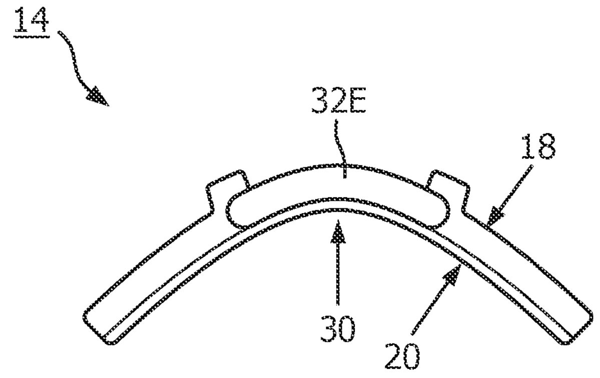
Figure 4C:
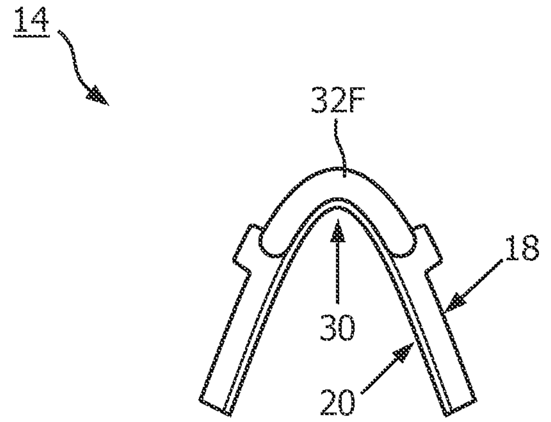

Through the use of inserts of different dimension and/or shape, one or both of the size and/or shape of deformable zone 30, and as a result frame 14, can be selectively varied to best fit a particular user. As an example, FIG. 3A shows, in simplified form, end views of three inserts $\mathbf{32}_A$-$\mathbf{32}_C$ of different widths $W_A$-$W_C$ which may be employed in frame 14 of mask 12 of FIG. 2 in order to generally adjust the width of the deformable zone. As another example, FIG. 3B shows, in simplified form, end views of three inserts 32$D_D$-$\mathbf{32}_F$ of varying curvature (i.e., having different values for a radius of curvature $R_c$) according to an example embodiment of the present invention which may be employed to generally adjust the curvature of deformable zone 30, as well as the general shape of frame 14. FIGS. 4A-4C, respectively, show, in simplified, slightly exaggerated form, top views (i.e., looking down toward the of frame 14 of mask 12 of FIG. 2 generally along the arrow of FIG. 2) with different ones of the three inserts $\mathbf{32}_D$-$\mathbf{32}_F$ of varying curvature (i.e., having different values for radius of curvature $R_c$) of FIG. 3B installed in deformable zone 30 of frame 14.

Figure 5:
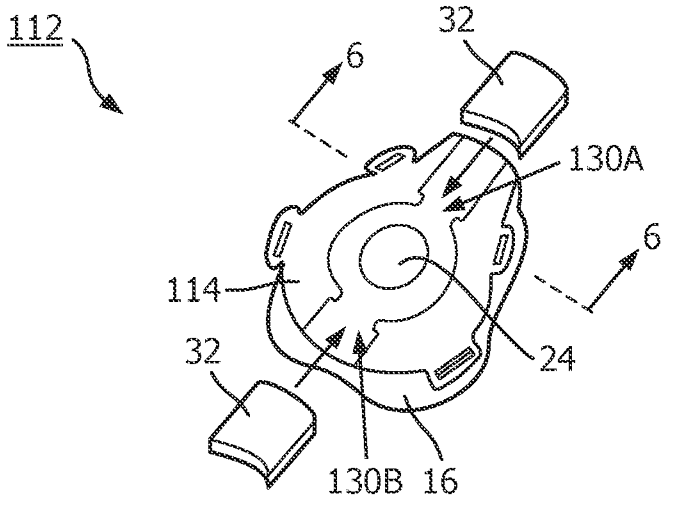
FIG. 5 is a partially exploded isometric view of a mask in accordance with another example embodiment of the present invention shown with two removable inserts shown exploded away from the frame of the mask.

Referring now to FIG. 5, a partially exploded isometric view of a mask 112 in accordance with another example embodiment of the present invention is shown with two removable inserts 132 shown exploded away from a frame 114. Mask 112 is of generally similar construction as mask 12 of FIGS. 1B and 2 except frame 114 of mask 112 includes two deformable zones 30A and 30B. A first deformable zone 30A is disposed at or about a portion of frame 114 which is structured to be disposed at or about the nose of the user when mask 112 is disposed on the face of the user. A second deformable zone 30B is disposed on an opposing side of opening 24 of frame 114 from first deformable zone 30A.

Figure 6A:
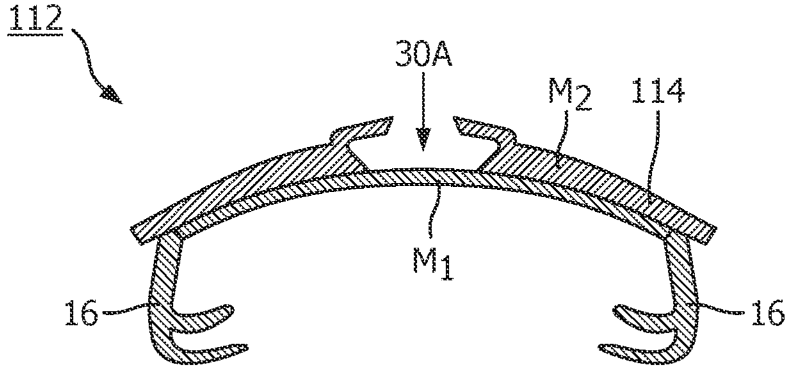
FIG. 6A is a sectional view of a portion of the mask of FIG. 5 in accordance with one example embodiment taken along line 6-6 of FIG. 5.

As shown in the sectional view of FIG. 6A, frame 114 may be formed in a similar manner as frame 14 previously discussed wherein deformable zone 30A (and similarly deformable zone 30B) is formed solely from a first, generally flexible first material $M_1$ (e.g., without limitation, silicone), and the remainder of frame 114 is formed from a second material $M_2$ which is different, and typically more rigid, than the first material. In an example embodiment of the present invention, each deformable zone 30A, 30B is formed from a portion a single unitary piece of material (e.g., without limitation, from a single continuous layer of silicone).

Figure 6B:
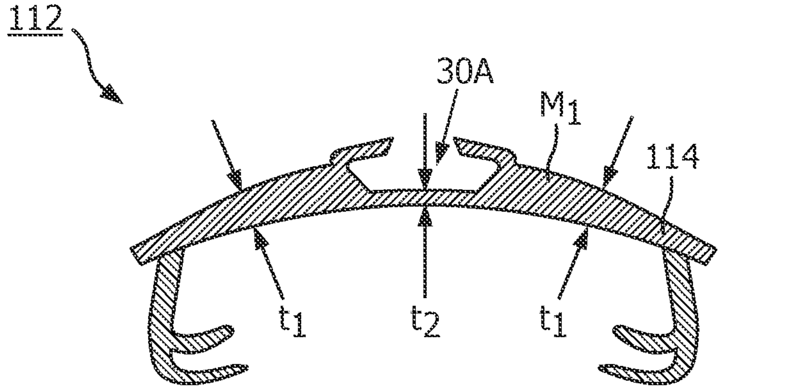
FIG. 6B is a sectional view of a portion of the mask of FIG. 5 in accordance with another example embodiment taken along line 6-6 of FIG. 5.

As shown in the sectional view of FIG. 6B, in an alternative embodiment frame 114 may be formed from a single material (e.g., without limitation, a semi-rigid plastic) wherein deformable zone 30A (and similarly deformable zone 130B) is formed as a thinned region in the first material. In the example shown in FIG. 6B, first material $M_1$ has a thickness $t_2$ which is much less than any thickness $t_1$ of the remainder portion of frame 114 outside of deformable zone 30A. In example embodiments of the present invention $t_2$ is less than 50% of $t_1$.

Figure 7A:
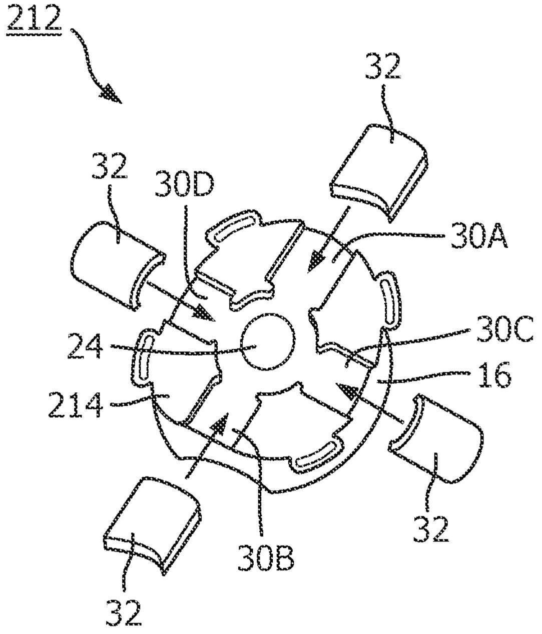
FIG. 7A is a partially exploded isometric view of a mask in accordance with an another example embodiment of the present invention shown with four removable inserts exploded away from the frame of the mask.
Figure 7B:
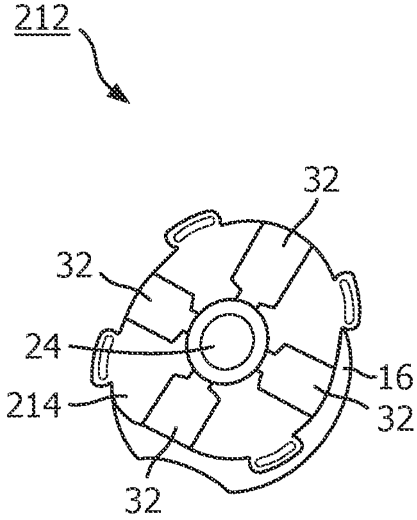
FIG. 7B is an isometric view of the mask of FIG. 7A shown with the four removable inserts coupled to the frame of the mask and an elbow coupling for connection to a flexible conduit coupled to the assembled mask.

Referring now to FIGS. 7A and 7B, a partially exploded and assembled isometric views of a mask 212 in accordance with yet another example embodiment of the present invention are shown. Mask 212 is similar to masks 12 and 112 previously discussed except that frame 214 of mask 212 includes four deformable zones 30A-30D. More particularly, frame 214 includes: a first deformable zone 30A disposed at or about a portion of the frame which is structured to be disposed at or about the nose of the user when the mask is disposed on the user; a second deformable zone 30B disposed about 180° about opening 24 from first deformable zone 30A; a third deformable zone 30C disposed about 90° about opening 24 from first deformable zone 30A; and a fourth deformable zone 30D disposed about 270° about opening 24 from first deformable zone 30A. Each of four deformable zones 30A-30D is structured to receive an insert 32 selectively coupled thereto.

Figure 8:
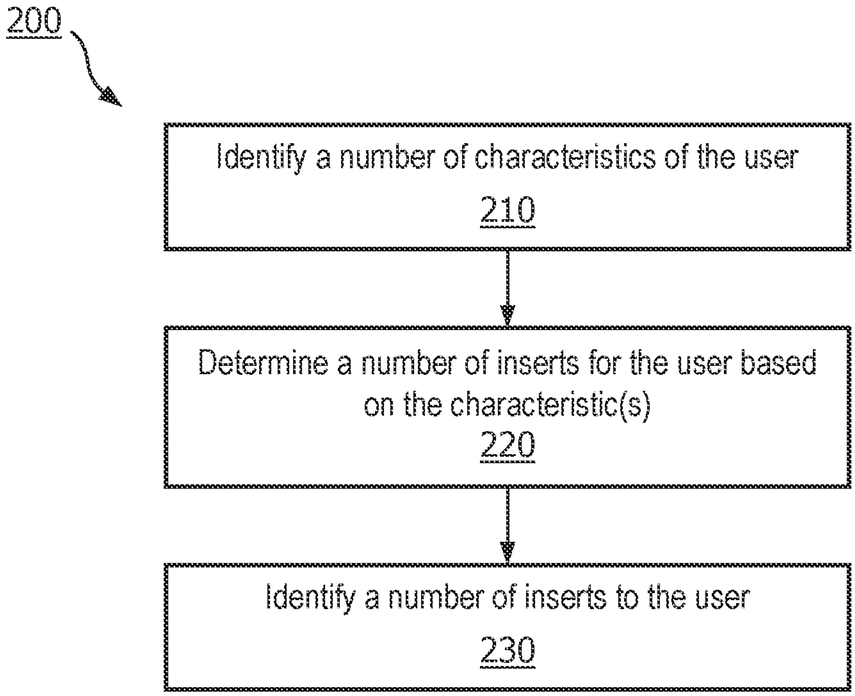
FIG. 8 is a flow chart showing the general steps of a method of sizing a customized mask to a user in accordance with an example embodiment of the present invention.

Having thus described several embodiments of masks in accordance with present invention, a method 200 of sizing a customized mask to a user will now be discussed in conjunction with FIG. 8. Method 200 begins at 210 by identifying a number of characteristics of the user. Such identifying may include obtaining information from the user, either in-person, or remotely. The information may include a number of facial dimensions of the user. The number of facial dimensions of the user may be obtained by questioning the patient regarding dimensional information (e.g., without limitation by having the user make measurements of features of their face—e.g., mouth width, nose, length, etc.). Alternatively, the number of facial dimensions of the user may be obtained by performing a facial scan of the user.

Next, at 220, the number of inserts for the user based on the number of characteristics is determined. During such determination the size or shape of each insert is determined for each deformable zone in the frame. Depending on the particular application (i.e., if multiple frame sizes or frames with different quantities of deformable zones are available), such step may involve first determining an appropriate frame for the user, and then determining the appropriate inserts therefore.

Finally, at 230, the number of inserts is identified to the user. Such indication may be carried out in a variety of ways. For example, without limitation, the inserts may be identified in an instruction sheet or via other suitable method so that the user can then locate and obtain the required insert(s). The number of insert may be provided to the user (either in person or shipped in a small package or via other suitable means). The number of inserts may be provided to the user installed in a mask, which is subsequently provided to the user (in such embodiments the method would include installation of the insert, e.g., sliding, snapping, etc., the inserts in place in the frame).

From the foregoing, it is to be appreciated that embodiments of the present invention provide for masks which can be custom fit to a user but at a much lower cost than other solutions which require costly equipment and time to produce. Additionally, unlike prior solutions, embodiments of the present invention may readily be re-customized to address changing needs or concerns of a patient.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment. It is also to be appreciated that the overall and/or cross sectional shapes of structures described herein are provided for exemplary purposes only and that such shapes may be varied without varying from the scope of the present invention.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A method of sizing a customized mask to a user, wherein the mask comprises (a) a frame having (1) a front face positioned to face away from the user when the mask is disposed on the face of the user; (2) a concave shaped rear face positioned to face toward the user when the mask is disposed on the face of the user, the rear face defining a cavity, the cavity being structured to receive a flow of a treatment gas therein and to receive at least one of a portion of a nose of the user and a mouth of the user therein; (3) an opening defined in a central portion of the frame, the opening passing between the front face and the rear face, the opening being structured to have a conduit coupled thereto for receiving the flow of the treatment gas; and (4) a number of deformable zones defined in the frame, each deformable zone being structured to receive a removable insert, each deformable zone being structured to adapt to at least one of a size or a shape of the removable insert received therein; (b) a conformable cushion coupled to the frame and structured to sealingly engage about at least one of at least a portion of the nose or the mouth of the user; and (c) a number of inserts, each insert configured to be selectively coupled in a respective deformable zone of the number of deformable zones and to cause deformation of the respective deformable zone, the method comprising:

identifying a number of characteristics of the user;

determining a number of the inserts for the user based on the number of characteristics; and identifying the number of inserts to the user.

2. The method of claim 1, wherein identifying the number of inserts to the user comprises providing the number of inserts to the user.

3. The method of claim 2, wherein providing the number of inserts to the user comprises: installing the number of inserts in the frame of the mask; and providing the mask to the user.

4. The method of claim 3, wherein installing the number of inserts in the frame of the mask comprises sliding each insert into the frame.

5. The method of claim 3, wherein installing the number of inserts in the frame of the mask comprises snapping each insert into the frame.

6. The method of claim 1, wherein identifying the number of characteristics of the user comprises obtaining information from the user.

7. The method of claim 6 wherein the information comprises a number of facial dimensions of the user.

8. The method of claim 7, wherein the number of facial dimensions of the user are obtained by questioning the patient regarding dimensional information.

9. The method of claim 7, wherein the number of facial dimensions of the user are obtained by performing a facial scan of the user.

* * * * *